US009433421B2

(12) United States Patent
Ueno et al.

(10) Patent No.: US 9,433,421 B2
(45) Date of Patent: Sep. 6, 2016

(54) SURGICAL TOOL FOR ANASTOMOSIS

(75) Inventors: Tomio Ueno, Yamaguchi (JP); Koji Suzuki, Hiroshima (JP); Hideyasu Miyahara, Hiroshima (JP)

(73) Assignees: JMS CO., LTD., Hiroshima (JP); YAMAGUCHI UNIVERSITY, Yamaguchi (JP)

(*) Notice: Subject to any disclaimer, the term of this patent is extended or adjusted under 35 U.S.C. 154(b) by 321 days.

(21) Appl. No.: 12/723,429

(22) Filed: Mar. 12, 2010

(65) Prior Publication Data
US 2011/0224705 A1 Sep. 15, 2011

(51) Int. Cl.
*A61B 17/11* (2006.01)
*A61B 17/04* (2006.01)
*A61B 17/06* (2006.01)
*A61B 17/062* (2006.01)

(52) U.S. Cl.
CPC ........ *A61B 17/1114* (2013.01); *A61B 17/0469* (2013.01); *A61B 17/062* (2013.01); *A61B 17/06166* (2013.01); *A61B 2017/1135* (2013.01)

(58) Field of Classification Search
CPC ............ A61B 17/30; A61B 2017/505; A61B 17/1114; A61B 17/0469; A61B 17/06166; A61B 17/062; A61B 17/122; A61B 17/1285; A61B 17/1227; A61B 17/28; A45D 26/0066; A61C 3/10; B25B 9/02; A61F 2/1664
USPC .......... 606/210, 205–208, 211, 151
See application file for complete search history.

(56) References Cited

U.S. PATENT DOCUMENTS

| | | | | | |
|---|---|---|---|---|---|
| 796,510 | A | * | 8/1905 | Hann | 606/210 |
| 1,612,606 | A | * | 12/1926 | Carlson | 30/248 |
| 1,767,296 | A | * | 6/1930 | Lewis | 7/168 |
| 1,869,295 | A | * | 7/1932 | Atterbury | 30/248 |
| 2,199,685 | A | * | 5/1940 | Wood | 606/210 |
| 2,291,413 | A | * | 7/1942 | Siebrandt | 606/103 |
| 2,584,547 | A | * | 2/1952 | Cahn | 606/133 |
| 3,906,957 | A | * | 9/1975 | Weston | 606/205 |
| 3,999,555 | A | * | 12/1976 | Person | 607/130 |
| 4,658,996 | A | * | 4/1987 | Warmath | 223/96 |
| 4,938,764 | A | * | 7/1990 | Glaberson | 606/131 |
| 4,944,741 | A | * | 7/1990 | Hasson | 606/206 |
| 4,950,275 | A | * | 8/1990 | Donini | 606/151 |
| 5,007,913 | A | * | 4/1991 | Dulebohn et al. | 606/107 |

(Continued)

FOREIGN PATENT DOCUMENTS

EP 1197184 A1 4/2002
JP Sho 61-137469 U 8/1986

(Continued)

OTHER PUBLICATIONS

Tomio Ueno, Development of Novel Method for Anastomosing and Anastomosis Assist Tool for Surgical Operation, Innovation Japan 2009 Presentation No. PW-26.

(Continued)

*Primary Examiner* — Dianne Dornbusch
(74) *Attorney, Agent, or Firm* — Pillsbury Winthrop Shaw Pittman, LLP

(57) ABSTRACT

A surgical tool has a body including a pair of legs, each leg having a leading edge and a butt end. The pair of legs are connected at their butt ends, wherein the pair of legs are configured to come close and depart at the leading edges. A deformable connecting member connects the pair of legs to one another at the leading edges.

20 Claims, 11 Drawing Sheets

(56) References Cited

U.S. PATENT DOCUMENTS

| | | | |
|---|---|---|---|
| 5,053,043 A | 10/1991 | Gottesman et al. | |
| 5,089,007 A * | 2/1992 | Kirsch et al. | 606/205 |
| 5,104,397 A * | 4/1992 | Vasconcelos et al. | 606/206 |
| 5,108,406 A * | 4/1992 | Lee | 606/106 |
| 5,167,618 A * | 12/1992 | Kershner | 604/22 |
| 5,217,473 A * | 6/1993 | Yoon | 606/157 |
| 5,261,918 A * | 11/1993 | Phillips et al. | 606/140 |
| 5,304,183 A * | 4/1994 | Gourlay et al. | 606/142 |
| 5,449,374 A * | 9/1995 | Dunn et al. | 606/208 |
| 5,509,923 A * | 4/1996 | Middleman et al. | 606/207 |
| 5,575,806 A * | 11/1996 | Nakao et al. | 606/207 |
| 5,584,855 A * | 12/1996 | Onik | 606/207 |
| 5,752,960 A * | 5/1998 | Nallakrishnan | 606/107 |
| 6,129,683 A * | 10/2000 | Sutton et al. | 600/564 |
| 6,139,563 A * | 10/2000 | Cosgrove et al. | 606/205 |
| 6,210,418 B1 * | 4/2001 | Storz et al. | 606/142 |
| 6,494,886 B1 * | 12/2002 | Wilk et al. | 606/142 |
| 6,863,679 B1 * | 3/2005 | Aaron | 606/210 |
| 7,235,073 B2 | 6/2007 | Levine et al. | |
| 7,404,821 B2 * | 7/2008 | Burbank et al. | 606/205 |
| 8,246,646 B2 * | 8/2012 | Kambin et al. | 606/192 |
| 8,578,589 B2 * | 11/2013 | Patterson | 29/559 |
| 2001/0044635 A1 * | 11/2001 | Niizeki et al. | 606/205 |
| 2003/0069600 A1 * | 4/2003 | Falahee | 606/205 |
| 2005/0070955 A1 * | 3/2005 | Young | 606/210 |
| 2006/0028040 A1 * | 2/2006 | Cohen et al. | 294/99.2 |
| 2008/0262539 A1 * | 10/2008 | Ewers et al. | 606/206 |
| 2009/0030424 A1 * | 1/2009 | Tuli et al. | 606/107 |
| 2011/0112568 A1 * | 5/2011 | Frecker et al. | 606/205 |

FOREIGN PATENT DOCUMENTS

| | | |
|---|---|---|
| JP | Sho 64-20837 A | 1/1989 |
| JP | Hei 4-20312 U | 2/1992 |
| JP | 04-263846 | 9/1992 |
| JP | Hei 11-19092 A | 1/1999 |
| JP | 2004-502488 A | 1/2004 |
| JP | 2006-175094 | 7/2006 |
| JP | 2007-301340 | 11/2007 |
| JP | 2007-307079 | 11/2007 |
| JP | 2009-050306 A | 3/2009 |
| JP | 2010-502325 A | 1/2010 |
| WO | 2007/116997 A1 | 10/2007 |

OTHER PUBLICATIONS

Japanese Office Action dated Nov. 26, 2013 of Japanese Patent Application No. 2010-054141.

* cited by examiner

Front end ← → Rear end

SURGICAL TOOL FOR ANASTOMOSIS

CROSS-REFERENCE TO RELATED APPLICATIONS

This application is related to prior Japanese Patent Application No. 2007-217212, filed Aug. 23, 2007, the entire contents of which are incorporated herein by reference.

FIELD OF THE INVENTION

This disclosure generally relates to surgical tools for anastomosis.

BACKGROUND

In a digestive system surgical operation, it is common to anastomose (to join by anastomosis) a duct or tube buried inside a parenchymal organ such as liver or pancreas with a hollow organ such as a digestive tract.

FIGS. 16A and 16B schematically show a conventional method for anastomosing a thin-diameter duct of a parenchymal organ to a digestive tract. As shown in FIGS. 16A and 16B, buried inside a pancreas P is a dead-end pancreatic duct D having an aperture formed on the cut end of the pancreas P. In order to communicate the pancreatic duct D with digestive tract K, this anastomosis operation begins by forming a small incision on the digestive tract K at a position aligned with the pancreatic duct D. Subsequently, a curved needle having a suture is vertically penetrated from its cut end into the pancreas P where the needle travels along its arc into the pancreatic duct D. The curved needle then passes through the duct D to penetrate from the small incision into the lumen of the digestive tract K. And then, the needle passes through the wall of the digestive tract K at the position opposing to the cut end of the pancreas P and travels through the tissue of pancreas P to reach duct D again. By repeating this procedure several times, the pancreas P is sutured to the side wall of the digestive tract K in the manner that the duct D can communicate with the lumen of the digestive tract through the small incision.

Such a thin diameter duct of a parenchymal organ makes anastomosis of the duct and another organ difficult. Using a magnifying glass or operating microscope does not overcome this difficulty because it is cumbersome to ensure a sufficient operating field around a thin-diameter duct, in particular when it is buried in a parenchymal organ. For a conventional anastomosis operation, a curved needle (which is, for example, 0.1 mm in diameter and 13 mm in length and ½ circle) connected to a suture is generally used. In a conventional anastomosis operation, a surgeon grips such a curved needle by use of a needle-carrier and drives the needle along its arc to place the connected suture at a desired position. However, it requires not only considerable surgical skill but also substantial time to precisely drive the needle without unduly invading a thin-diameter duct and surrounding parenchymal organ.

Japanese Patent Publication Number H04-263846 discloses one type of a conventional anastomosis auxiliary tool. The disclosed tool is directed to a surgical suture guide that can be used by surgeons without requiring advanced training. The tool comprises a hard metal portion having a slit for guiding a needle. The hard metal portion is inserted from an external urethral meatus into a urinary duct to facilitate an anastomosis operation for urethral alveolares. Thus, the disclosed tool can be used for anastomosing a tube only when the tube is exposed from surrounding tissues. While this type of anastomosis auxiliary tool can be used for anastomosing a movable urethral tube by inserting the tool in a retrograde fashion from a thick-diameter external urethral meatus to a position where the urethral tube is connected to another tissue, it would be difficult to arrange the disclosed tool into a dead-end thin-diameter duct of a parenchymal organ which has lower mobility.

Thus, the conventional anastomosis auxiliary tool cannot be applied to procedures for anastomosing a dead-end thin-diameter duct of a parenchymal organ with a hollow organ such as a digestive duct. Particularly, it is difficult to ensure that a suture is arranged at a desired position for anastomosis in a thin-diameter duct. Accordingly, there is a need to provide a surgical tool to assist a surgeon in effectively anastomosing such a dead end duct without unduly invading a surrounding tissue of a parenchymal organ.

SUMMARY

Various embodiments disclosed herein relate to a surgical tool, and more particularly relate to anastomosis auxiliary tools for anastomosing thin-diameter duct inside of a parenchyma organ to a hollow organ such as a digestive tract. In one aspect, the surgical tool comprises a body having a pair of legs, each leg having a leading edge and a butt end, the pair of legs being connected to at the butt ends, wherein the anastomosis auxiliary tool is configured for anastomosing a dead-end thin-diameter duct of a parenchymal organ with a hollow organ without unduly invading a surrounding tissue of the parenchymal organ. In another aspect, the surgical tool, in accordance with various embodiments, comprises a body having a pair of legs, each having the leading edge and a butt end, the pair of legs being connected to at the butt ends, wherein the pair of legs are configured to come close and depart at the leading edges; and a deformable connecting member connecting, either directly or indirectly, the pair of legs at the leading edges. In another aspect, the pair of legs may be configured to elastically deform such that the pair of legs come closer to and depart from one another. In another aspect, the connecting portion of the pair of legs may be formed into a hinge structure around which the pair of legs come closer to and depart from one another.

In another aspect, the surgical tool comprises a ring surrounding the pair of legs, wherein the ring surrounds the pair of legs in a slidable manner in an axial direction of the pair of legs and the ring is configured to apply a pressure on the pair of legs inwardly. The ring may be formed into any type of members including a circular or rectangular ring that can accommodate the pair of legs therethrough and apply an inward pressure on the pair of legs.

In another aspect, the surgical tool comprises a pair of slope portions extending forward from each of the leading edges of the pair of legs in a tilted manner with respect to the axis of the pair of legs; and a pair of forefront portions extending forward from each of the leading edges of the pair of slope portions in the direction substantially parallel to the axis of the pair of legs; wherein the connecting member connects the pair of forefront portions at their leading edges. Each one of the pair of slope portions may be any type of member that is attached to the pair of legs in a tilted manner with respect to the axis of the pair of legs so that a surgeon can ensure a sufficient operating field from the direction of the butt end of the surgical tool. Each of the pair of forefront portions may be any type of member which can support the connecting member and be inserted into a thin-diameter duct of an organ together with the connecting member in accordance with an operator's operation.

According to various embodiments, the connecting member may be made of a flexible material. In another aspect, the connecting member is configured to deform in response to a pressure less than a minimum pressure required to deform either the pair of legs, pair of slope portions or forefront portions.

In another aspect, the surgical tool comprises one or more projections formed on at least one of the pair of forefront portions. In another aspect, the one or more projections are formed on at least one of outward surfaces of the pair of forefront portions. In another aspect, the one or more projections are arranged in an equally spaced manner. In another aspect, a rear end of each of the one or more projections projects higher than a corresponding front end of each of the one or more projections.

In another aspect, an angle between a central axis of each of the pair of slope portions and the central axis of the each of the pair of legs is between 20° and 80°. The central axis of each of the pair of slope portions extends substantially in parallel with a longitudinal axis of each of the pair of slope portions. The central axis of each of the pair of legs extends substantially in parallel with a longitudinal axis of each of the pair of legs. In another aspect, each leg further comprises a fore end portion that is configured to be detachable from the rear end portion. In another aspect, the pair of forefront portions are configured to be detachable from the pair of slope portions. In another aspect, the pair of slope portions are configured to be detachable from the pair of legs.

Various embodiments disclosed herein relate to a replaceable surgical unit. The replaceable surgical unit, in accordance with various embodiments, comprises a pair of forefront portions configured to be detachable from a base end unit of a surgical tool; and a deformable connecting member connecting the pair of forefront portions at leading edges of the pair of forefront portions; wherein the base end unit includes: a pair of legs being connected to one another at butt end of the pair of legs, wherein the pair of legs are configured to elastically deform such that the legs come closer to and depart from one another; and a pair of slope portions extending forward from each of the leading edges of the pair of legs in a tilted manner with respect to a central axis of each of the pair of legs; wherein the pair of forefront portions are configured to be attached to the pair of slope portions such that the pair of forefront portions extend in a direction parallel with a central axis of the each of pair of legs.

Various embodiments disclosed herein relate to a method for placing a suture with a surgical tool comprising a body having a pair of legs and a deformable connecting member connecting, either directly or indirectly, the pair of legs at the leading edges. The method, in accordance with various embodiments, comprises: deforming the surgical tool such that the pair of legs are in a closed configuration where the pair of legs are in contact with one another; inserting, with the pair of legs in the closed configuration, the surgical tool into a thin-diameter duct of a parenchymal organ such that at least the connecting member is inside the thin-diameter duct; deforming the surgical tool such that the pair of legs are in an open configuration where the pair of legs are apart from one another; passing a curved needle connected to a suture through a loop defined at least by the connecting member and the pair of legs; and drawing back the surgical tool from the thin-diameter duct.

In another aspect, drawing back the surgical tool comprising drawing back the suture from the thin-diameter duct by engaging the suture with the connecting member. In another aspect, the surgical tool is inserted at a depth same as or more than the length of the curved needle. In another aspect, the curved needle is pierced into the parenchymal organ from cut end of the parenchymal organ. In another aspect, the curved needle is driven inside tissue of the parenchymal organ along arc of the curved needle. In another aspect, the drawn back suture is severing.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

With reference to the drawings, a surgical tool according to one embodiment is described herein. The surgical tool may be herein referred to as a anastomosis auxiliary tool. In this disclosure, the term of "surgical tool" can be used interchangeably with "anastomosis auxiliary tool".

Figure 1A:
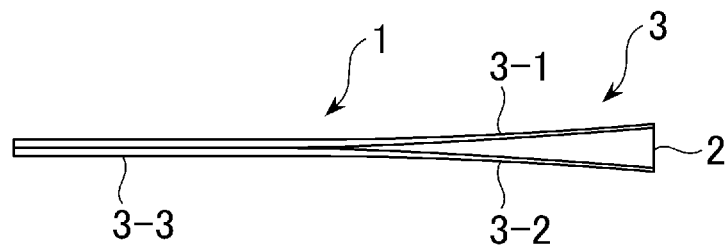
FIG. 1A shows an illustrative embodiment of an anastomosis auxiliary tool where a pair of legs are apart from one another.
Figure 1B:
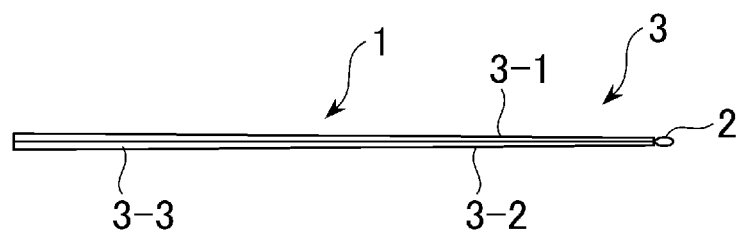
FIG. 1B shows an illustrative embodiment of an anastomosis auxiliary tool where a pair of legs are in contact with one another.

First looking at FIG. 1A, there is shown an anastomosis auxiliary tool 1 where legs 3-1 and 3-2 are apart from one another; and FIG. 1B shows the anastomosis auxiliary tool 1 where legs 3-1 and 3-2 are in contact with one another. Referring to FIGS. 1A and 1B, anastomosis auxiliary tool 1 comprises a linear flexible member 2 and pole member 3. The pole member 3 is formed of a pair of resilient metal legs 3-1 and 3-2. The rear end or butt end of the leg 3-1 is fixedly connected to the rear end or butt end of the leg 3-2 such that the legs 3-1and 3-2 are formed into V shape where their leading edges are apart from one another. The leading edges of legs 3-1 and 3-2 means the foremost edges thereof each of which the linear flexible member is attached. It should be noted that any portion where the legs 3-1 and 3-2 are connected to one another may be called a rear end or butt end even if any other portions are attached to the legs 3-1 and 3-2 from their rear end side and, therefore the rear end or butt end are not rear end of the entire surgical tool 1. The leading ends of the legs 3-1 and 3-2 are reduced in diameter as compared to their butt ends so that the leading edge can penetrate into a thin-diameter duct. The flexible member 2 is formed of a soft metal or plastic member with a diameter of 0.3-1.0 mm and bridges the leading edges of legs 3-1 and 3-2 to provide a loop between the pair of legs 3-1 and 3-2. The linear member (also referred to as a flexible member) 2 is extended, as shown in FIG. 1A, when the leading ends of legs 3-1 and 3-2 of pole member 3 depart from one another. On the other hand, the flexible member 2 could be coiled or looped, as shown in FIG. 1B, when legs 3-1 and 3-2 are transformed to be in contact with one another. Thus, the legs 3-1 and 3-2 may be elastically deformed such that the legs 3-1 and 3-2 come closer to and depart from one another about the butt end portion. The flexible member 2 is tough enough not to be severed or disengaged from the leading edges of legs 3-1 and 3-2 while it is drawn back from a thin-diameter tube in engagement with a suture as described below.

As noted above, the leading edge of the legs 3-1 and 3-2 can penetrate into a thin-diameter duct. A duct buried inside a parenchymal organ such as an intrahepatic bile duct or a pancreatic duct can be categorized into 2 groups: a thin-diameter duct having diameter ranging from 3-4 millimeters; and an extremely-thin-diameter duct having diameter ranging from 1-2 millimeters. In order to anastomose a thin-diameter duct with a digestive tract, surgeons use a needle carrier to drive a needle for anastomosing a thin-diameter duct and a digestive tract. As used herein, such a thin-diameter duct and an extremely-thin-diameter duct may be collectively referred to as a "thin-diameter duct."

Figure 1C:
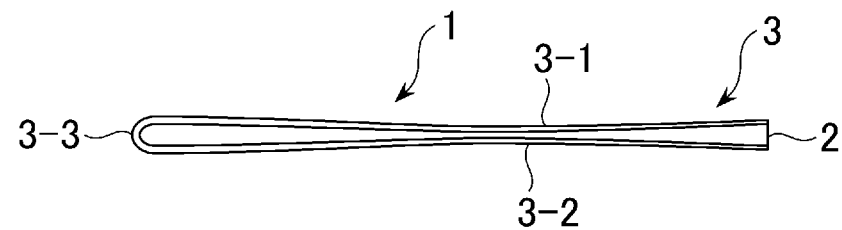
FIG. 1C shows another example of an anastomosis auxiliary tool according to various embodiments.

Referring next to FIG. 1C, there is shown is another example of anastomosis auxiliary tool 1 where pole member 3 is formed into substantially U shape. The anastomosis auxiliary tool 1 shown of FIG. 1C comprises a pair of legs 3-1, 3-2, each made of a metal resilient material, which are connected to one another at 3-3, i.e., the rear end or butt end of the tool 1. As with the example shown in FIG. 1A, the leading edges of legs 3-1 and 3-2 are reduced in diameter as compared to their butt ends.

Although FIGS. 1A-1C show examples of auxiliary tool 1 where the butt end portion of pole member 3 is configured to be gripped by a surgeon in operation, it should be appreciated that a separate grip member may be attached to the but end of pole member 3.

Figure 2A:
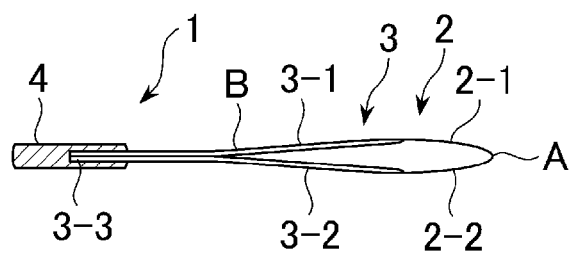
FIG. 2A shows another example of an anastomosis auxiliary tool according to various embodiments where a pair of legs are apart from one another.
Figure 2B:
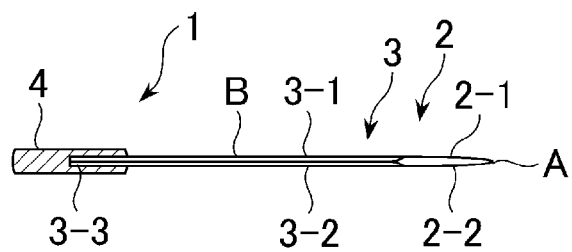
FIG. 2B shows an illustrative embodiment of the anastomosis auxiliary tool of FIG. 2A where a pair of legs are in contact with one another.

Now referring to FIGS. 2A and 2B, another example of anastomosis auxiliary tool according to various embodiments will be described. FIG. 2A shows an anastomosis auxiliary tool 1 according to various embodiments where legs 3-1 and 3-2 are apart from one another; and FIG. 2B shows the anastomosis auxiliary tool 1 where the legs 3-1 and 3-2 are in contact with one another. The anastomosis auxiliary tool 1 of FIGS. 2A and 2B comprises a flexible members 2, pole member 3 and grip member 4. Flexible member 2 is formed into substantial U shape by folding, at peak A, a flexible linear wire with a diameter of 0.3-1.0 mm. Each of linear members 2-1 and 2-2 is made of flexible material such as plastic or metal. The anastomosis auxiliary tool 1, in response to pressure applied to the butt end of pole member 3, is transformed from its open configuration as shown in FIG. 2A into its closed configuration as shown in FIG. 2B. In the closed configuration, the tool 1 is inserted into a thin-diameter duct of a parenchymal organ. The flexible member 2 may be made of a material stiff enough not to be folded, in inserting the tool 1 into a thin-diameter duct of a parenchymal organ, by pressure from the inner wall of the thin-diameter duct. Additionally, the flexible member 2 is tough enough not to be severed or disengaged from the leading edges of legs 3-1 and 3-2 while it is drawn back from a thin-diameter tube in engagement with a suture. The leading edge of flexible member 2 may be formed into a round shape, not a pointed shape.

Continuing to refer to FIGS. 2A and 2B, the pole member 3 comprises a pair of resilient legs 3-1 and 3-2, which are fixedly connected to one another at their butt ends 3-3. The leading edge of pole member 3 is formed into substantial V shape in a open configuration where there is no pressure applied to the pole member 3. When legs 3-1 and 3-2 are made of a stiff material, the connecting portion of legs 3-1 and 3-2 may be formed into a hinge structure wherein a spring member (not shown) may be disposed on the inner walls thereof around center B. The leading edges of legs 3-1 and 3-2 are smoothly connected with corresponding linear members 2-1 and 2-2 so that the legs 3-1 and 3-2 can be smoothly inserted into a thin-diameter duct. For this purpose, each of legs 3-1 and 3-2 may be formed to have the same diameter as that of corresponding linear members 2-1 and 2-2. In another embodiment, the butt end of pole member 3 may be formed into substantial U shape by smoothly connecting legs 3-1 and 3-2 to one another where the pole member 3 may be formed integral with the flexible member 2 and made of resilient plastic material. Alternatively, pole member 3 may be formed as a separate part from flexible member 2. In this case, the pole member 3 may be made of a different material from flexible member 2.

The butt end of pole member 3 may be housed inside cylindrical grip member 4, which is shown in FIGS. 2A and 2B using a cross-sectional view thereof.

When an operator applies pressure onto legs 3-1 and 3-2 around center B, the legs 3-1 and 3-2 are transformed from an open configuration as shown in FIG. 2A to a closed configuration as shown in FIG. 2B, which also transforms the linear members 2-1 and 2-2 to a closed configuration. In such a closed configuration, the flexible member 2 and pole member 3 are inserted into a thin-diameter duct.

Figure 3A:
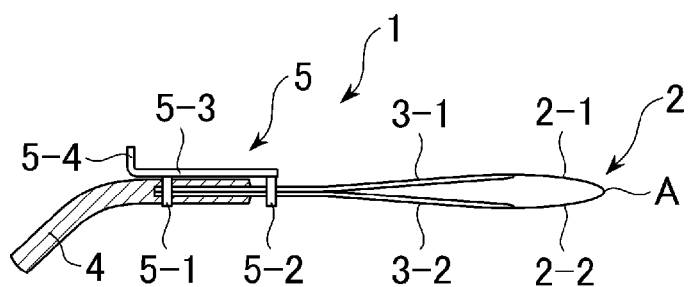
FIG. 3A shows another example of an anastomosis auxiliary tool according to various embodiments where a pair of legs are apart from one another.
Figure 3B:
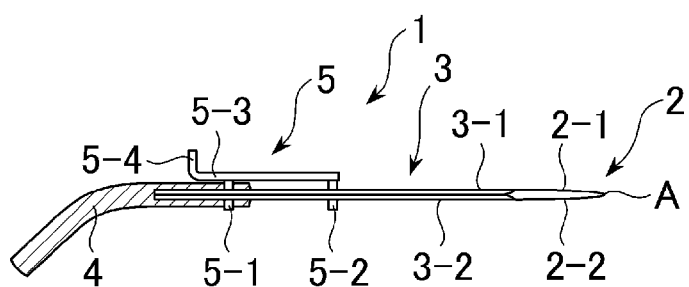
FIG. 3B shows an illustrative embodiment of the anastomosis auxiliary tool of FIG. 3A where a pair of legs are in contact with one another.

Referring next to FIGS. 3A and 3B, various embodiments will be explained. FIG. 3A shows another example of anastomosis auxiliary tool according to various embodiments where legs 3-1 and 3-2 are apart from one another; and FIG. 3B shows the anastomosis auxiliary tool where legs 3-1 and 3-2 are in contact with one another. The anastomosis auxiliary tool 1 of FIGS. 3A and 3B is formed by adding operating portion 5 to the tool 1 of FIG. 2 and modifying the grip member 4 to extend diagonally backward. The operating portion 5 comprises a first ring 5-1 surrounding the grip member 4 in a slidable manner along the axis thereof, second ring 5-2 surrounding the butt end portion of the pole member 3 in a slidable manner along the axis thereof; connecting portion 5-3 connecting the first ring 5-1 and second ring 5-2 and extending backward from the position opposing the first ring 5-1; and curved portion 5-4 formed at the rear end of the connecting portion 5-3. In operation, there is provided a anastomosis auxiliary tool in an open configuration as shown in FIG. 3A. An operator grips the grip member 4 of the tool 1 and presses curved portion 5-4 to shift the second ring 5-2 forward. By shifting the second ring 5-2 forward, an inward pressure is applied onto the legs 3-1 and 3-2, which transforms the tool 1 in a closed configuration. Each portion included in the operating portion 5 is made of a metal or hard plastic material stiff enough to deform legs 3-1 and 3-2 in response to an applied pressure.

Figure 4A:
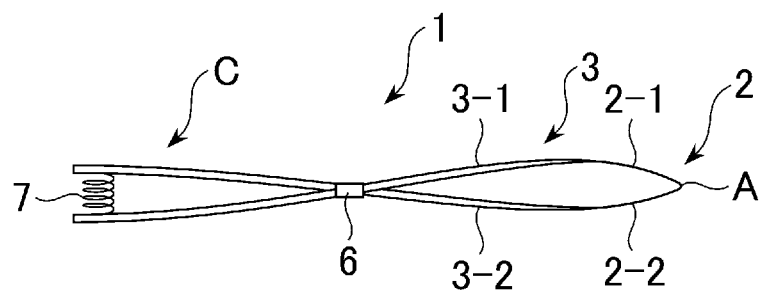
FIG. 4A shows another example of an anastomosis auxiliary tool according to various embodiments where a pair of legs are apart from one another.
Figure 4B:
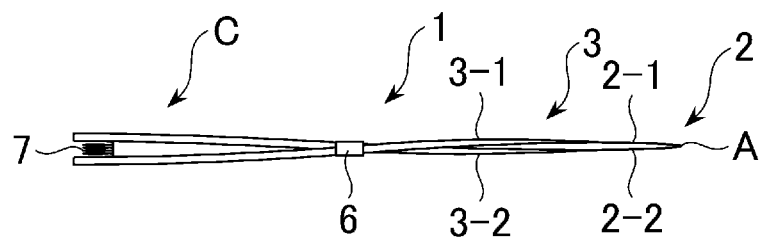
FIG. 4B shows an illustrative embodiment of the anastomosis auxiliary tool of FIG. 4A where a pair of legs are in contact with one another.
Figure 4C:
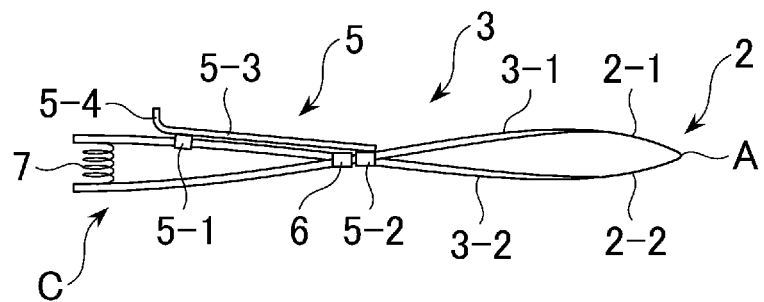
FIG. 4C shows another example of an anastomosis auxiliary tool according to various embodiments.

Referring next to FIGS. 4A-4C, there is shown another example of an anastomosis auxiliary according to various embodiments. As shown in FIG. 4A, anastomosis auxiliary tool 1 comprises a pole member 3 including legs 3-1 and 3-2 being arranged to cross one another where the legs 3-1 and 3-2 are pivotally supported by ring 6 provided around the intersection thereof. Such a configuration pivotable around the ring 6 allows the legs 3-1 and 3-2 to be transformed between an open configuration shown in FIG. 4A and a closed configuration shown in FIG. 4B. The ring 6 may be made of a circular wire or resilient plastic material. Instead of the ring 6, the legs 3-1 and 3-2 may be supported by a pin provided at the intersection of the legs 3-1 and 3-2. In this case, the intersection may be formed to have a wide portion so as to accommodate the pin.

Attached inside the butt end of the legs 3-1 and 3-2 is a spring 7 which is designed to apply an outward pressure onto the legs 3-1 and 3-2. The pressure from the spring 7 allows the anastomosis auxiliary tool 1 to be in an open configuration as shown in FIG. 4A in the condition where there is no external pressure is applied thereto. In operation, an operator presses grip portion C inwardly against spring pressure from the spring member 7 to transform the anastomosis auxiliary tool 1 into a closed configuration as shown in FIG. 4B.

FIG. 4C shows another aspect of anastomosis auxiliary tool 1. The anastomosis auxiliary tool 1 as shown in FIG. 4C is formed by attaching operating portion 5 onto anastomosis auxiliary tool 1 as shown in FIGS. 4A and 4B. Operating portion 5 is formed in substantially the same manner as operating portion 5 as shown in FIGS. 3A and 3B.

Figure 5:
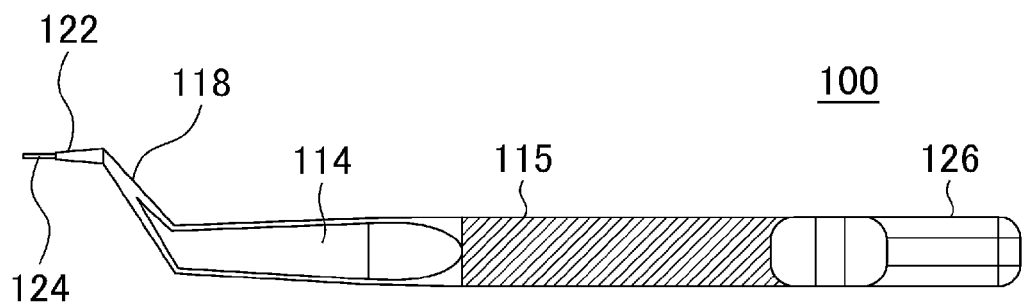
FIG. 5 shows an elevation view of an illustrative embodiment of a surgical tool according.
Figure 6:
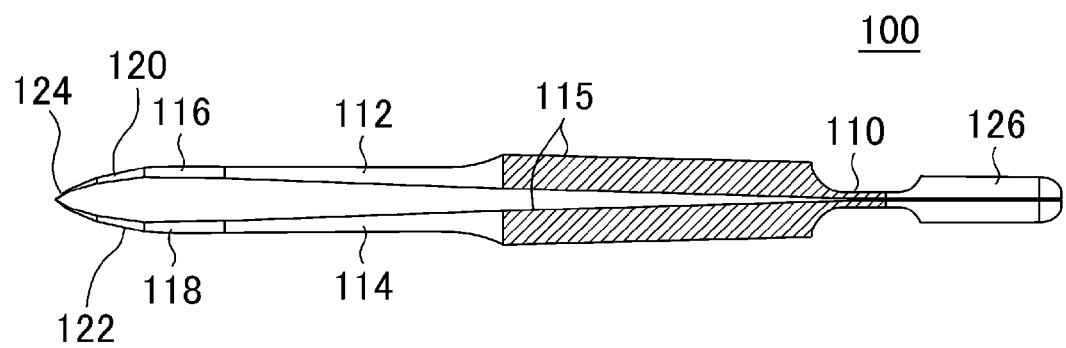
FIG. 6 shows a top plan view of the surgical tool of FIG. 5 where a pair of legs are apart from one another.
Figure 7:
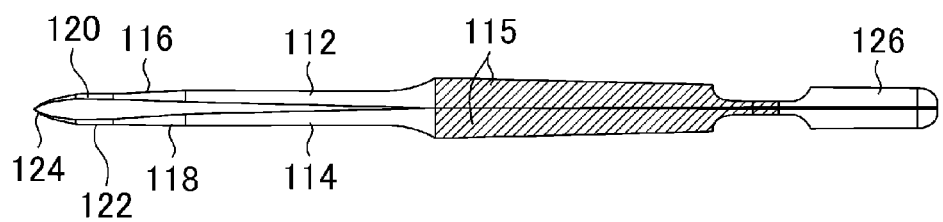
FIG. 7 shows a top plan view of the surgical tool of FIG. 5 where a pair of legs are in contact with one another.

Referring now to FIGS. 5-9, various embodiments of a surgical tool will be described. FIGS. 5-7 show a surgical tool 100 according to various embodiments. The surgical tool 100 may be used to arrange a suture in an appropriate position of a thin-diameter duct of an organ (e.g., a main pancreatic duct) to anastomose such a duct to another organ such as an intestinal tract.

The surgical tool 100 comprises a pair of legs 112 and 114 which are connected to one another at butt end portion 110; a pair of slope portions 116 and 118 each of which is connected to the corresponding leading edge of the corresponding legs 112 and 114; a pair of forefront portions 120 and 122 each of which is connected to the corresponding leading edge of the corresponding slope portions 116 and 118; connecting member such as flexible member 124 for connecting the forefront portions 120 and 122 at their leading edges; and balancer 126 for adjusting the barycentric position of the surgical tool 100. The balancer 126 is attached to the rear edge of butt end portion 110. The surgical tool 100 may be configured to be 160 mm in length from its leading edge (i.e., the leading edge of flexible member 124) to butt end (i.e., the rear edge of balancer 126).

Formed onto each of the legs 112 and 114 is a grip portion 115 which is designed to be gripped by a surgeon in a surgical operation. In response to an operation via the grip portion 115, the legs 112 and 114 may be elastically deformed such that the legs 112 and 114 come closer to and depart from one another about the butt end portion 110. More particularly, if there is no external pressure applied thereon, the legs 112 and 114 maintain an open configuration where the legs 112 and 114 are apart from one another due to their inherent elasticity, as shown in FIG. 6. In the event grip portion 115 is pressed inwardly by a surgeon, the legs 112 and 114 elastically come closer to one another and eventually get transformed into a closed configuration where the legs 112 and 114 come in contact with each other, as shown in FIG. 7. The grip portion 115 is formed into a sheet shape measuring 10.5 mm wide and 5.25 mm thick. Each of the leading edge portion of the legs 112 and 114 (i.e., a portion of the legs 112 and 114 which is interposed between the leading edge of the grip portion 115 and the corresponding slope portion 116 and 118) is formed into a sheet shape measuring 10.5 mm wide and 2.2 mm thick. Each of the legs 112 and 114 is reduced in diameter at their respective leading edges where legs 112 and 114 are connected to corresponding slope portions 116 and 118. The leading edges of legs 112 and 114 means the foremost edges thereof where the elongated axes of legs 112 and 114 terminate.

Referring still to FIGS. 5-7, each of the slope portions 116 and 118 extends forward (towards the leading edge of the surgical tool 100) from each of the leading edges of the corresponding legs 112 and 114 in a tilted manner with respect to the axis of the legs 112 and 114. The angle between the both axes may be between 20° and 80°. Shown in FIG. 5 is an example where the angle is set to 55°. Each of the slope portions are formed to get thinner as approaching their respective leading edge.

Each of the forefront portions 120 and 122 extends forward from each of the leading edges of the corresponding slope portions 116 and 118 in the direction substantially parallel to the axis of the corresponding legs 112 and 114. Each of the forefront portions 120 and 122 is formed into a flat sheet shape having proper size to be inserted into a pancreatic duct and formed to get thinner as approaching their respective leading edges. For instance, by taking into account various factors such as the size of a standard pancreatic duct, the length from its leading edge to rear edge which is connected to slope portions 116 or 118 may be set to 15 mm and the diameter of a portion within 5.0 mm from the leading edge of each of the forefront portions 120 and 122 may be set to below 1.0 mm so as to be smoothly inserted into a pancreatic duct. In one embodiment, each of the forefront portions 120 and 122 may be formed into a curved shape curving inwardly as approaching theirs respective leading edges.

Figure 8:
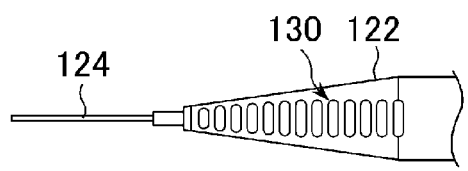
FIG. 8 shows an enlarged elevation view of an illustrative embodiment of forefront portions and a flexible portion provided in the surgical tool of FIG. 5.
Figure 9:
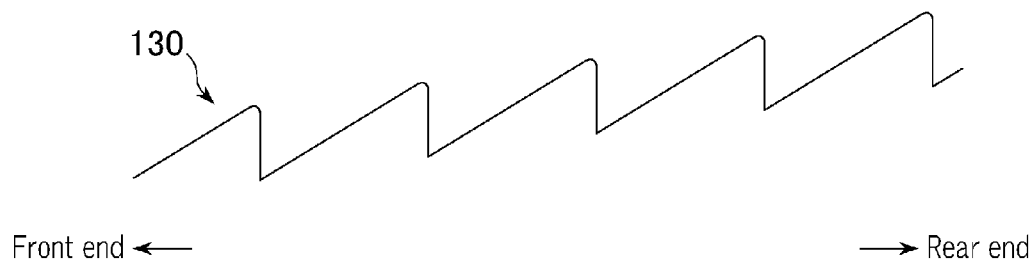
FIG. 9 shows an enlarged top plan view of an illustrative embodiment of projection members formed on the surgical tool of FIG. 5.

As shown in FIG. 8, formed on at least one of the outward surfaces of the forefront portions 120 and 122 are one or more projection members 130. If there are multiple projection members 130 arranged in an equally spaced manner from their respective leading edges, such projection members 130 permit to measure a length from the leading edges of the forefront portions 120 and 122 to one of the multiple projections 130. As shown in FIG. 9, the rear ends of each projection members 130 are formed in substantially a perpendicular manner with respect to the outward surface of the forefront portions 120 and 122, whereas the front ends are formed in a titled manner with respect to the outward surface. As such, the rear end portions of each of the projection members 130 project higher than the corresponding front end portions thereof. The peaks of each projection member 130 is tapered to prevent invading a pancreas in operation.

The flexible member 124 is made of a metal wire measuring 10 mm long and 0.3-1.0 mm thick. The wire may be made of stainless steel and is folded on its center into a substantial V shape to form flexible member 124. Alternatively, flexible member 124 may be made of a plastic linear material. The both ends of the folded wire (flexible member 124) are attached to the leading edges of the forefront portions 120 and 122. The flexible member 124 is formed to be more flexible compared to the legs 112, 114, slope portions 116, 118 and forefront portions 120, 122 so that the flexible member 124 can follow the deformation of the legs 112 and 114 in response to a pressure thereto. That is, the flexible member 124 is configured to deform in response to a pressure less than a minimum pressure required to deform either the pair of legs 112 and 124, pair of slope portions 116 and 118 or forefront portions 120 and 122. As such, in response to a pressure applied to the legs 112 and 114, the flexible member 124 may be selectively transformed into an open configuration as shown in FIG. 6 or closed configuration as shown in FIG. 7. Although the above embodiment uses flexible member 124 to bridge the forefront portions 120 and 122, it should be noted that the leading edges of the forefront portions 120 and 122 may be connected to one another by any type of materials (e.g., a string which is made of natural or chemical fiber) deformable in response to a pressure operation onto the legs 112 and 114.

In one embodiment, fore end portions of the legs 112 and 114 may be detachable from the rear end portions thereof. In one embodiment, each the fore end portions of the legs 112 and 114 is a portion which interpose between the fore end of the grip member 115 and rear end of the slope portions 116 and 118. For instance, fore end portions of the legs 112 and 114 may be detached at the fore end of the grip member 115. Additionally or alternatively, the slope portions 116 and 118 may be configured either integral with or detachable from the corresponding legs 112 and 114. Furthermore, the forefront portions 120 and 122 may be configured either integral with or detachable from the corresponding slope portions 116 and 118. Such detachable forefront portions 120 and 122 may be attached to the corresponding slope portions 116 and 118 such that the forefront portions 120 and 122 extend in the direction parallel with the axis of the legs 112 and 114. The sizes and configurations of the forefront portions 120 and 122 vary depending on what type of organs are anastomosed by use of the surgical tool 1. If forefront portions 120 and 122 are provided separately from the other elements of the surgical tool 100, such separate forefront portions 120 and 122 may have various sizes and configurations in accordance with particular applications. By selectively exchanging such separately-provided forefront portions 120 and 122, a resulting surgical tool 100 may be used for various organs which may have different sizes. Forefront portions 120 and 122 and flexible member 124 may be made of a plastic material so that they can be disposable, which results in reducing time spent on lavaging surgical tool 100 and preventing the connecting member such as flexible member 124 from being damaged due to lavaging.

As noted above, forefront portions 120 and 122 according to various embodiments are arranged at the position upwardly shifted from the axis of legs 112 and 114. As such, when a surgeon uses surgical tool 100 to arrange a suture at a desired position, legs 112 and 114 does not hinder the surgeon's vision. Thus, surgical tool 100 according to various embodiments facilitates securing surgical field around an organ to be anastomosed.

With reference next to FIGS. 10A through 14B, there is shown one illustrative example of a series of procedures to place a suture at a desired position for anastomosing a main pancreatic duct T of a pancreas P to a side wall of an intestinal tract K using surgical tool 100 in accordance with various embodiments. It should be appreciated that anastomosis auxiliary tool 1 as shown in FIGS. 1A through 4C may also be used in substantially the same manner as the surgical tool 100 for placing a suture at a desired position. Thus, the following descriptions are only exemplary.

Figure 10A:
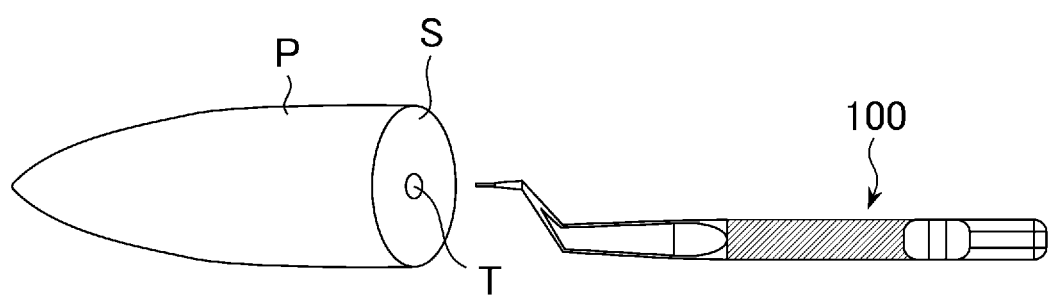
FIGS. 10A-13C show an exemplary procedure for arranging a suture according to various embodiments.
Figure 10B:
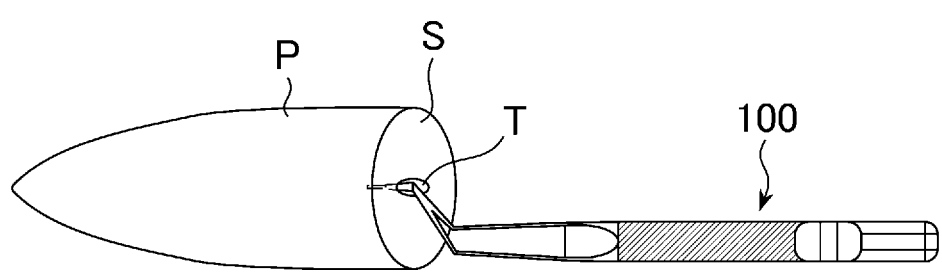
Figure 11A:
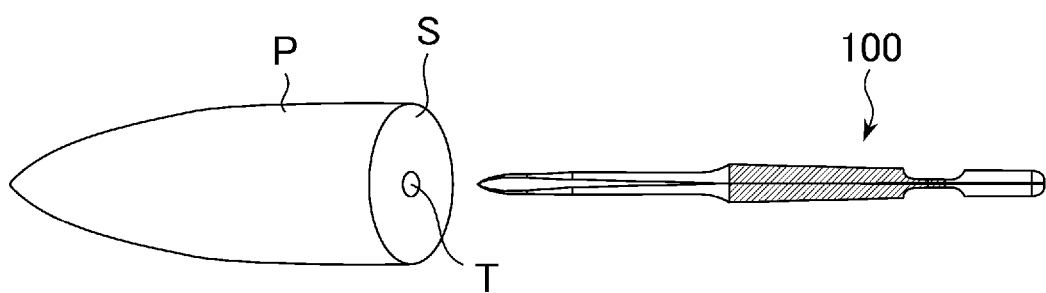
Figure 11B:
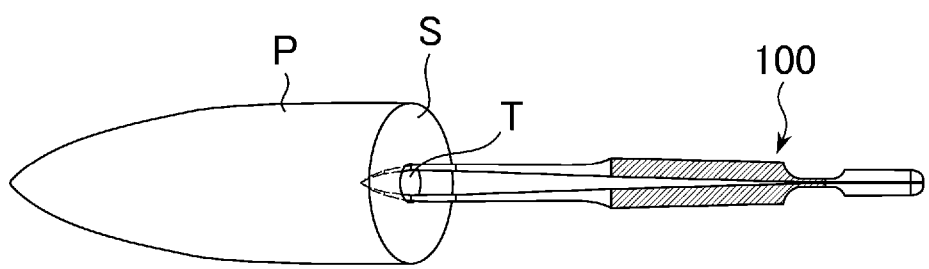

First, a surgeon holds grip portion 115 to maintain surgical tool 100 in a closed configuration as shown in FIGS. 10A and 11A and then, with the surgical tool 100 in that closed configuration, direct the surgical tool 100 toward the pancreas P to insert flexible member 124 and forefront portions 120 and 122 into main pancreatic duct T to a desired depth. The leading edge of the flexible member 124 is inserted into the duct T from cut end S, for example, to a depth same as or more than the length of curved needle N. The length of the curved needle N means the length of the chord connecting the both ends of the needle N. The curved needle N may be formed into an arc shape having a diameter of 0.1 mm and a circumference of 10-20 mm. If it is determined that the surgical tool 100 has been inserted into the duct T to a desired depth, the surgeon eases the pressure on the grip portion 115 to allow the legs 112 and 114 to depart from one another due to their inherent resiliency. Such a deformation of the legs 112 and 114 causes the forefront portions 120 and 122 also to depart from one another, resulting in flexible member 124 into an open configuration. Each side of the flexible member 124 departs from one another until they encounter inner wall of the duct T. As such, the flexible member 124 is arranged inside the main pancreatic duct T along its inner wall, wherein the flexible member 124 and forefront portions 120 and 122 apply an outward pressure onto the inner wall of the duct T to deform the cross section of the duct T into a ellipse shape, as shown in FIGS. 10B and 11B. Such main pancreatic duct T being deformed into such an ellipse shape facilitates an operation of driving the needle N from cut end S into the duct T, as compared to a natural shape of the duct T as shown in FIGS. 10A and 10B.

Figure 12A:
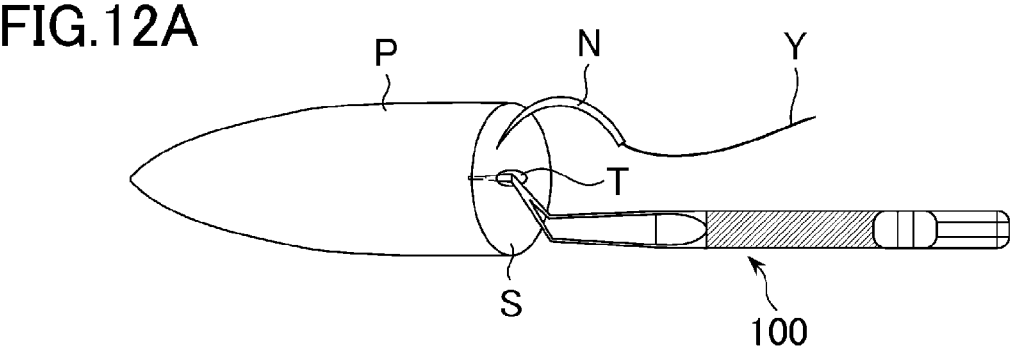
Figure 12B:
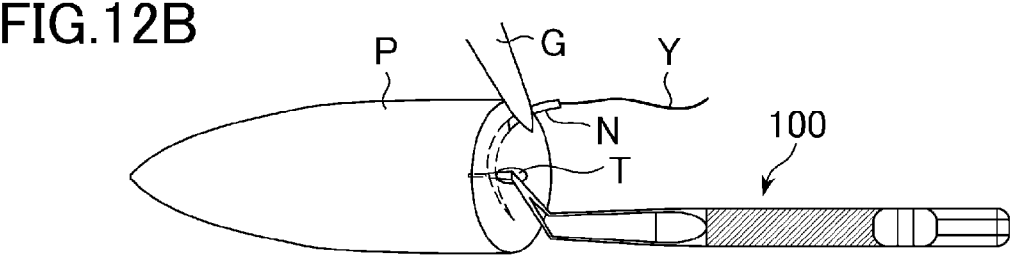
Figure 12C:
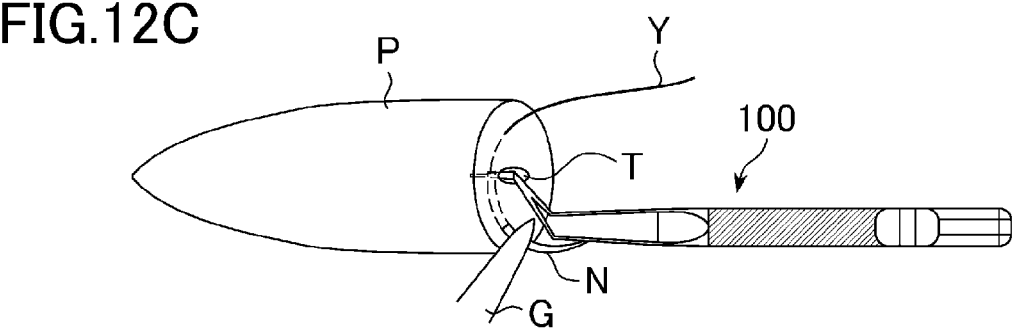
Figure 12D:
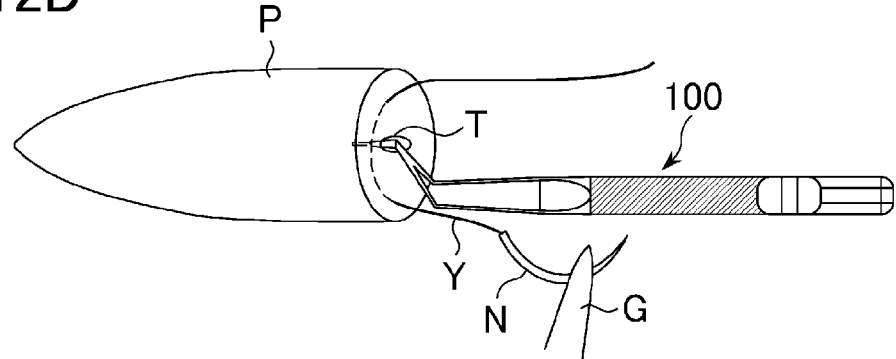

Subsequently, as shown in FIGS. 12A and 12B, the surgeon uses a needle carrier G to grab the curved needle N connected to a suture Y and pierces the needle N into the pancreas P from its cut end S. Then, the curved needle N travels along its arc through the pancreatic tissue and emerges into the main pancreatic duct T. Upon emerging into the duct T, the needle N passes through the loop defined by the flexible member 124 and the forefront portions 120 and 122 before again penetrating from the opposite inner wall of the duct T into the pancreatic tissue. The needle N advances through pancreas P along its arc as shown in FIG. 12C, and finally emerges from the cut end S, as shown in FIG. 12D.

Figure 13A:
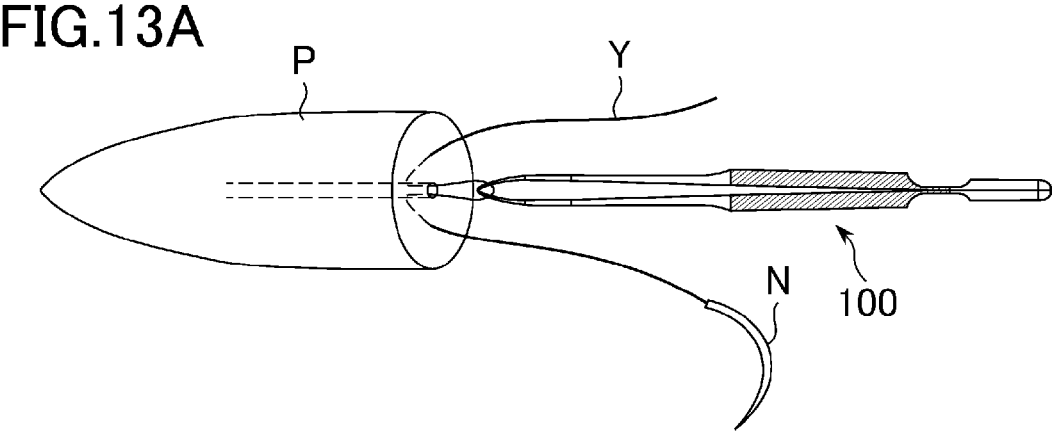
Figure 13B:
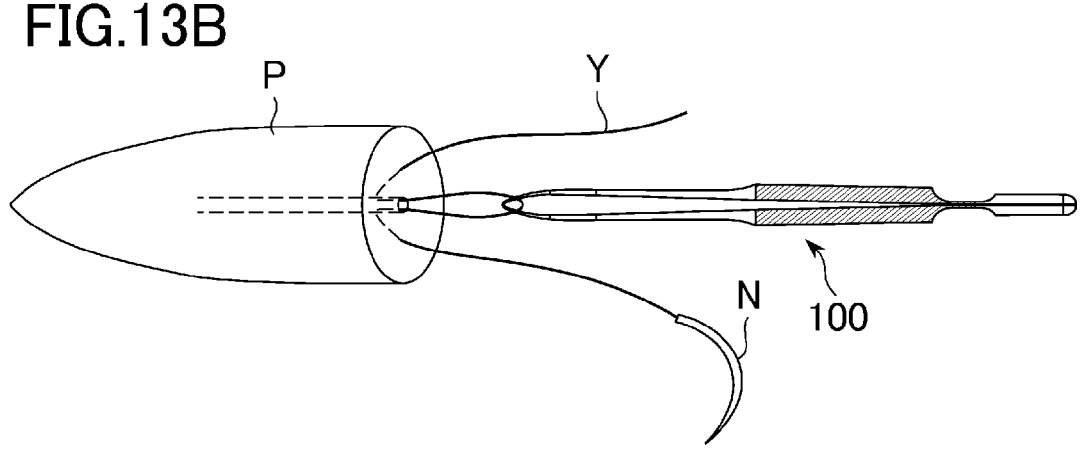
Figure 13C:
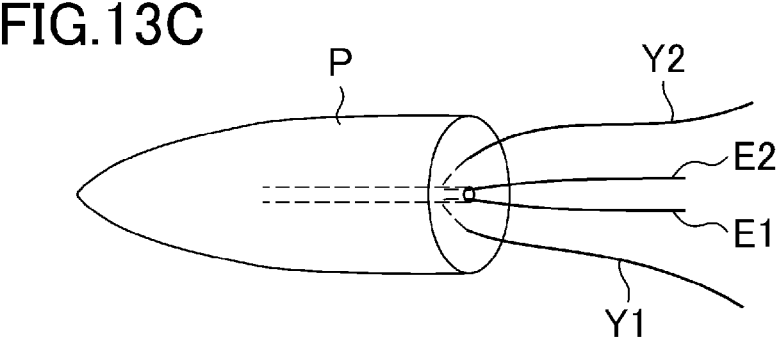

Subsequently, the flexible member 124 and forefront portions 120 and 122 are drawn back outside the main pancreatic duct T as shown in FIGS. 13A and 13B. The suture Y connected to the needle N is also drawn back by virtue of the engagement with the tip end of the flexible member 124. Once drawn back, the suture Y is severed, at a portion adjacent to the tip end of the flexible member 124, into first suture Y1 and second suture Y2 and the needle N is detached from the suture Y. Thus, a pair of severed sutures Y1 and Y2 are arranged such that their respective one ends are placed adjacent to the opening of the main pancreatic duct T and the other ends pass through the inner wall of the duct T and emerges from the cut end S. If a deformable member such as a thread is used in place of the flexible member 124 in operation, such a deformable member is tough enough not to be severed as it is drawn back from the main pancreatic duct T.

According to various embodiments, the curved needle N can naturally travel through the pancreas P along its arc, which prevents unduly invading surrounding tissue of the pancreas P. Without using surgical tool 100 according to various embodiments, in order to place a connected suture at a desired position adjacent to the opening of the main pancreas duct T, a conventional curved needle has to travel through a pancreas off the path defined by its arc, resulting in significantly invading tissues of the pancreas. Alternatively, a conventional curved needle having smaller arc can naturally travel through pancreas P towards the opening of the main pancreatic duct T and, therefore, can place a suture at a desired position adjacent to the opening. However, such a small curved needle cannot penetrate into sufficient depth of pancreas P as compared to a larger curved needle, which could cause anastomotic insufficiency such as failed anastomosis. As compared to such conventional procedures, the above-described procedures according to various embodiments, by virtue of the surgical tool 100, may facilitate placing a suture at a desired position using a large curved needle without unduly invading pancreas P.

Figure 14A:
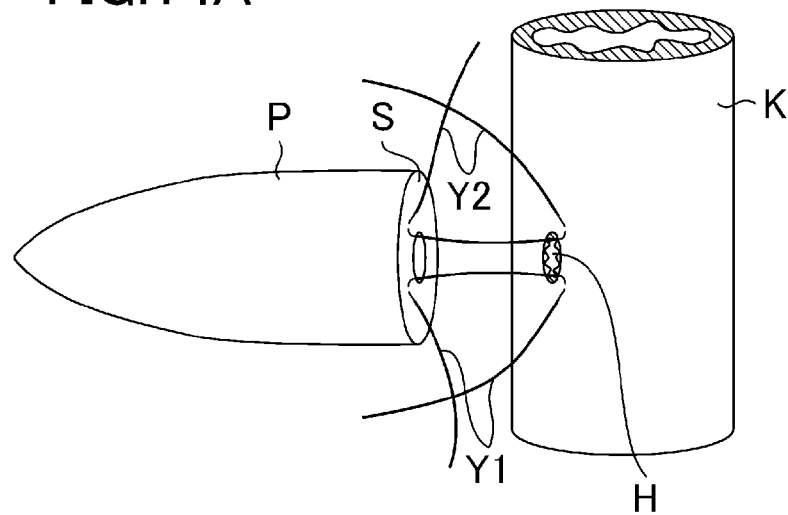
FIGS. 14A and 14B show an exemplary anastomosis using the surgical tool of FIG. 5.
Figure 14B:
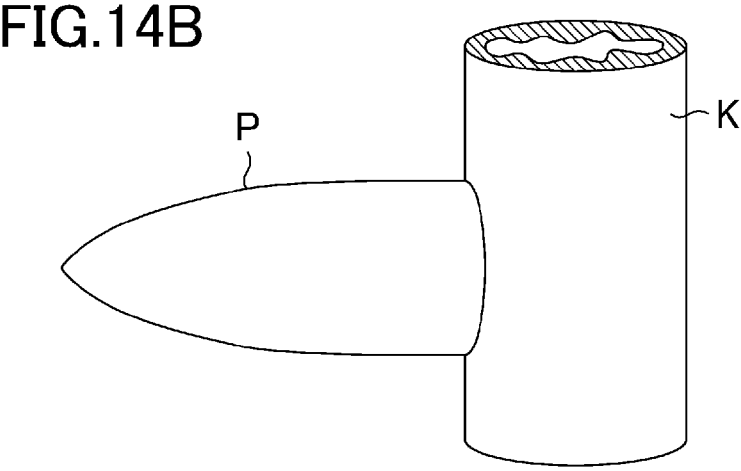
Figure 15:
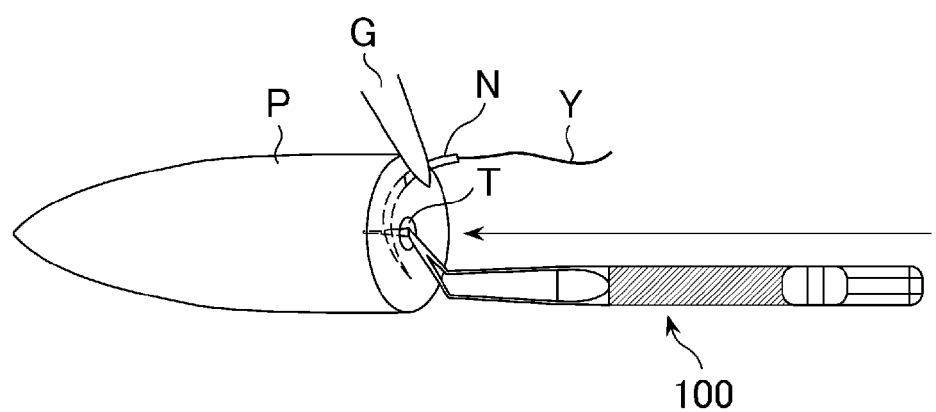
FIG. 15 shows a schematic layout of the surgical tool of FIG. 5 in the anastomosis.
Figure 16A:
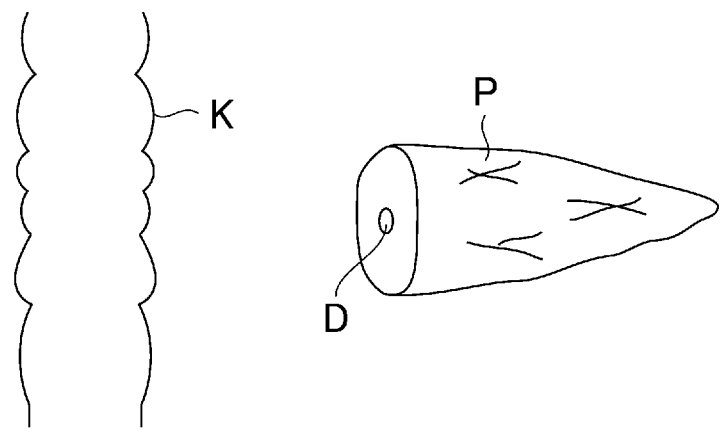
FIGS. 16A and 16B show a conventional anastomosis.
Figure 16B:
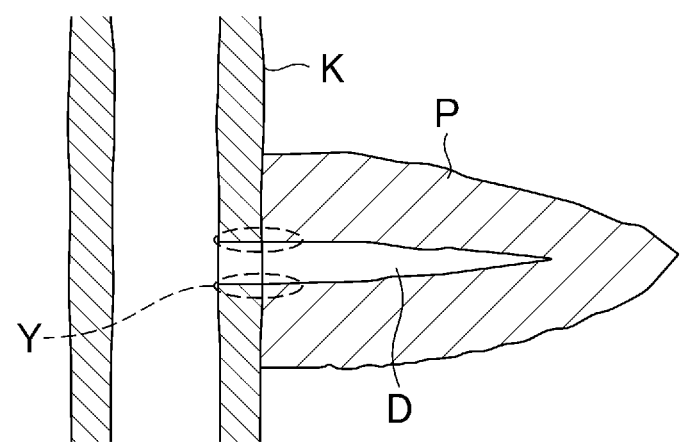

Upon placing the suture Y at a desired position adjacent to the opening of the main pancreatic duct T, an anastomosis procedure begins by connecting a pair of needles (not shown) to cut ends E1 and E2 of respective sutures Y1 and Y2. As shown in FIG. 14A, once the opening of the main pancreatic duct T is aligned with small hole (or small incision) H made on the side wall of intestinal tract K, the needle attached to the suture Y1 passes through the small hole H to penetrate into the lumen of the intestinal tract K and then pierce through the side wall of the intestinal tract K from the inside thereof, resulting in emerging from the side wall of intestinal tract K. Once emerging from the intestinal tract K, the needle is detached from the first suture Y1 in preparation for later procedures. The same procedure is conducted for the suture Y2. As a result, the sutures Y1 and Y2 are arranged such that they respectively penetrate from the cut end S into the pancreas P to travel therethrough to the main pancreatic duct T, and run through the duct T up to the small hole H, and then finally pass through the hole H to enter into the intestinal tract K and pierce through the side wall of the track K to emerge from the side wall thereof.

The above procedures described with reference to FIGS. 10-14 is repeatedly conducted several times to place a plurality of sutures in substantially the same manner as threads Y1 and Y2. Once such a plurality of sutures (e.g. 8 sutures) are placed at the desired position, a surgeon tightens those sutures to join the cut end S with the side wall of the intestinal tract K, as shown in FIG. 14B, so as to communicate the opening of main pancreatic duct T with the small hole H, which permits pancreatic fluid from pancreas P to flow from the main pancreatic duct T into the lumen of intestinal tract K.

In the procedures of arranging sutures at a desired position described above with reference to FIGS. 12 and 13, a surgeon tries to ensure a sufficient operating field from the direction of the butt end of the surgical tool 100. According to various embodiments, the forefront portions 120 and 122 and flexible member 124 are arranged at the position upwardly shifted from the axis of legs 112 and 114, which allows a surgeon to acquire a sufficient surgical field around the opening of main pancreatic duct T without being hindered by the legs 112 and 114.

According to various embodiments, one or more projection members 130 which are formed on at least one of the outward surfaces of the forefront portions 120 and 122 may prevent surgical tool 100 from dropping off the main pancreatic duct T during the operation of FIG. 12. Particularly, the rear ends of the projection members 130 which are formed in a substantially perpendicular manner with respect to the outward surface of forefront portions 120 and 122 further help surgical tool 100 be retained inside main pancreatic duct T during the operation. Additionally or alternatively, since the front ends of the projection members 130 are formed in a titled manner with respect to the outward surface of forefront portions 120 and 122, the tilted portion can work as a guide for guiding the forefront portions 120 and 122 inside the main pancreatic duct T. Furthermore, a set of multiple projection members arranged in an equally spaced manner from their respective leading edges enable to measure a length from the leading edges of forefront portions 120 and 122 to one of the multiple projections, which facilitates determining whether the flexible member 124 is inserted to a sufficient depth.

The present disclosure is not to be limited in terms of the particular embodiments described in this application, which are intended as illustrations of various aspects. Many modifications and variations can be made without departing from its spirit and scope, as will be apparent to those skilled in the art. For example, although the above examples are described using the example of anastomosis of main pancreatic duct T with intestinal tract K, it should be noted that surgical tool 100, with appropriate modifications thereto, may be used to anastomose any type of parenchyma organs with any type of hollow organs or join any type of hollow organs with one another. Hollow organs to be anastomosed include any type of digestive tract such as pharynx, esophagus, stomach, intestine duodenum, jejunum, large intestine and rectum. Furthermore, surgical tool 100 may be used to anastomose, for example, tracheas, blood vessels, urinary duct, and fallopian tube with one another. Surgical tool 100 may be modified in stiffness, elasticity, material, size, or configuration of each element thereof to accommodate various organs. Curved needle N may be modified such that, for example, its arc has more or less than a half circle.

The invention claimed is:

1. A surgical tool comprising:
a body having a pair of legs, each leg having a leading edge and a butt end, the pair of legs being directly connected together at the butt ends, wherein the pair of legs are configured to come close to each other and depart away from each other at the leading edges; and
a deformable connecting wire having opposing ends thereof connected directly to the leading edges of the pair of legs and extending forwardly therefrom, the wire having a linear configuration along the entire length between the opposing ends thereof,
wherein the deformable connecting wire is folded so as to have a peak that extends forwardly away from the leading edges in a direction opposite to the connected butt ends when the leading edges of the pair of legs are both close to and departed away from each other, the folding of the wire enabling peak-first insertion thereof into a thin-diameter duct of parenchymal organ, wherein the connection of the opposing ends of the wire to the leading edges of the legs enables portions of the wire extending between the peak and the leading edges to be moved towards and away from each other together with the leading edges moving towards and away from each other, respectively.

2. The surgical tool of claim 1, further comprising:
a ring surrounding the pair of legs, wherein the ring surrounds the pair of legs in a slidable manner in an axial direction of the pair of legs and the ring is configured to apply a pressure on the pair of legs inwardly.

3. The surgical tool of claim 1, wherein the deformable connecting wire comprises a diameter of approximately 0.3 mm to approximately 1.0 mm.

4. The surgical tool of claim 1, wherein the wire is integrally formed and connected smoothly with the leading edges of the pair of legs for smooth insertion into the thin-diameter duct of the parenchymal organ.

5. A surgical tool comprising:
a body having a pair of legs, each leg having a leading edge and a butt end, the pair of legs being directly connected together at the butt ends,
a pair of slope portions, each slope portion extending forward from each of the leading edge of the pair of legs in a tilted manner with respect to a central axis of each of the pair of legs;
a pair of forefront portions, each forefront portion extending forward from each of the slope portions in the direction substantially parallel to the central axis of each of the pair of legs; and
a wire having opposing ends thereof connected directly to the leading edges of the pair of forefront portions and extending forwardly therefrom, the wire having a linear configuration along the entire length between the opposing ends thereof, the wire being folded so as to have a peak that extends forwardly away from the leading edges of the pair of forefront portions in a direction opposite to the connected butt ends when the leading edges of the pair of legs are in contact with each other and when the leading edges of the pair of legs are apart from one another, the folding of the wire enabling peak-first insertion thereof into a thin-diameter duct of parenchymal organ, wherein the connection of the opposing ends of the wire to the leading edges of the pair of forefront portions enables portions of the wire extending between the peak and the leading edges of the pair of forefront portions to be moved towards and away from each other together with the leading edges of the pair of forefront portions moving towards and away from each other, respectively.

6. The surgical tool of claim 5, wherein the wire is made of a flexible material.

7. The surgical tool of claim 6, wherein the wire is configured to deform in response to a pressure less than a minimum pressure required to deform either the pair of legs, pair of slope portions or forefront portions.

8. The surgical tool of claim 5, further comprising one or more projections formed on at least one of the pair of forefront portions.

9. The surgical tool of claim 8, wherein the one or more projections are formed on at least one of outward surfaces of the pair of forefront portions.

10. The surgical tool of claim 8, wherein the one or more projections are arranged in an equally spaced manner.

11. The surgical tool of claim 8, wherein a rear end of each of the one or more projections projects higher than a corresponding front end of each of the one or more projections.

12. The surgical tool of claim 5, wherein an angle between a central axis of each of the pair of slope portions and the central axis of each of the pair of legs is between 20° and 80°.

13. The surgical tool of claim 5, wherein each leg further comprises a fore end portion that is configured to be detachable from a rear end portion.

14. The surgical tool of claim 5, wherein each leg further comprises a fore end portion that is configured to be detachable from the slope portion.

15. The surgical tool of claim 5, wherein the pair of slope portions are configured to be detachable from the pair of legs.

16. The surgical tool of claim 5, wherein the wire comprises a thickness of approximately 0.3 mm to approximately 1.0 mm.

17. The surgical tool of claim 5, wherein the wire is integrally formed and connected smoothly with the leading edges of the pair of forefront portions for smooth insertion into the thin-diameter duct of the parenchymal organ.

18. A replaceable surgical unit comprising:
a pair of forefront portions configured to be detachable from a base end unit of a surgical tool; and
a deformable connecting wire having opposing ends thereof connected directly to leading edges of the pair of forefront portions and extending forwardly therefrom, the wire having a linear configuration along the entire length between the opposing ends thereof;
wherein the base end unit includes:
a pair of legs being connected to one another at butt ends of the pair of legs, wherein the pair of legs are configured to elastically deform such that the legs come closer to and depart from one another; and
a pair of slope portions extending forward from each of the leading edges of the pair of legs in a tilted manner with respect to a central axis of each of the pair of legs;
wherein the pair of forefront portions are configured to be attached to the pair of slope portions such that the pair of forefront portions extend in a direction parallel with a central axis of each of the pair of legs,
wherein the deformable connecting wire is folded so as to have a peak that extends forwardly away from the leading edges of the pair of forefront portions in a direction opposite to the connected butt ends when the pair of legs are both closer to and departed away from one another, the folding of the wire enabling peak-first insertion thereof into a thin-diameter duct of parenchymal organ, and
wherein the connection of the opposing ends of the wire to the leading edges of the pair of forefront portions enables portions of the wire extending between the peak and the leading edges of the pair of forefront portions to be moved towards and away from each other together with the leading edges of the pair of forefront portions moving towards and away from each other, respectively.

19. The replaceable surgical unit of claim 18, wherein the deformable connecting wire comprises a diameter of approximately 0.3 mm to approximately 1.0 mm.

20. The replaceable surgical unit of claim 18, wherein the wire is integrally formed and connected smoothly with the leading edges of the pair of forefront portions for smooth insertion into the thin-diameter duct of the parenchymal organ.

* * * * *